(12) United States Patent
Lindsay et al.

(10) Patent No.: US 9,006,282 B2
(45) Date of Patent: Apr. 14, 2015

(54) ROSUVASTATIN AND ATORVASTATIN DERIVATIVES

(71) Applicant: Redx Pharma Limited, Manchester (GB)

(72) Inventors: Derek Lindsay, Wigan (GB); Peter Jackson, Wigan (GB); Stephen Hindley, Wigan (GB); Inder Bhamra, Wigan (GB)

(73) Assignee: Redx Pharma Limited, Manchester (GB)

( * ) Notice: Subject to any disclaimer, the term of this patent is extended or adjusted under 35 U.S.C. 154(b) by 0 days.

(21) Appl. No.: 13/944,195

(22) Filed: Jul. 17, 2013

(65) Prior Publication Data

US 2013/0303773 A1 Nov. 14, 2013

Related U.S. Application Data

(63) Continuation of application No. 13/255,700, filed as application No. PCT/GB2010/050407 on Mar. 10, 2010, now Pat. No. 8,513,412.

(30) Foreign Application Priority Data

Mar. 10, 2009 (GB) .................................. 0904104.7

(51) Int. Cl.
*C07D 405/06* (2006.01)
*A61K 31/40* (2006.01)
*A61K 31/506* (2006.01)
*C07D 405/14* (2006.01)

(52) U.S. Cl.
CPC .............. *C07D 405/06* (2013.01); *A61K 31/40* (2013.01); *A61K 31/506* (2013.01); *C07D 405/14* (2013.01)

(58) Field of Classification Search
CPC ... A61K 31/40; A61K 31/506; C07D 405/06; C07D 405/14
See application file for complete search history.

(56) References Cited

U.S. PATENT DOCUMENTS

| 4,681,893 A | 7/1987 | Roth | |
|---|---|---|---|
| 2007/0043221 A1* | 2/2007 | Moody et al. | 548/517 |

FOREIGN PATENT DOCUMENTS

| EP | 0409281 | | 7/1990 |
|---|---|---|---|
| EP | 0521471 | | 1/1993 |
| EP | 1834944 | | 9/2007 |
| EP | WO2007/107276 | * | 9/2007 |
| WO | WO 2005/012246 | | 2/2005 |
| WO | WO 2005/092867 | | 10/2005 |
| WO | WO 2006/122644 | | 11/2006 |
| WO | WO 2010/103319 | | 9/2010 |
| WO | WO 2010/103320 | | 9/2010 |

OTHER PUBLICATIONS

Banwell et al. (J. Org. Chem. 1988, 63, 9139-9144).*
Baker, S. and Tarnopolsky, M., "Satin myopathies: pathophysiologic and clinical perspectives," Clin Invest Med., 24(5):258-272, (Oct. 2001).
Haleblian, J., "Characterization of habits and crystalline modification of solids and their pharmaceutical applications," J Pharm Sci, 64(8):1269-1288, (Aug. 1975).
Hamelin, B. and Turgeon, J., "Hydrophilicity/lipophilicity: relevance for the pharmacology and clinical effects of HMG-CoA reductase inhibitors," Trends in Pharmacological Sciences, 19(1):26-37, (Jan. 1, 1998).
Tararov, V., et al., "Synthesis of the chiral side of chain of statins—lactone versus lactol pathway," European Journal of Organic Chemistry, 24:5543-5550, (Dec. 2006).
International Search Report cited in International Application No. PCT/GB2010/050407 mailed May 7, 2010.
International Search Report cited in International Application No. PCT/GB2010/050408 mailed May 4, 2010.
International Search Report cited in International Application No. PCT/GB2010/050409 mailed May 3, 2010.
Souillac et al. Characterization of Delivery Systems, Differential Scanning Calorimetry, pp. 217-218 (in Encyclopedia of controlled Drug delivery, 1999, John Wiley & Sons, pp. 212-227).
Vippagunta et al. Advanced Drug Delivery Reviews, 2001, 48: pp. 3-26.

* cited by examiner

*Primary Examiner* — Valerie Rodriguez-Garcia
(74) *Attorney, Agent, or Firm* — Greenberg Traurig, LLP; Chinh H. Pham; Natalie Salem

(57) ABSTRACT

This invention relates to the discovery of novel rosuvastatin and atorvastatin analogues.

26 Claims, 1 Drawing Sheet

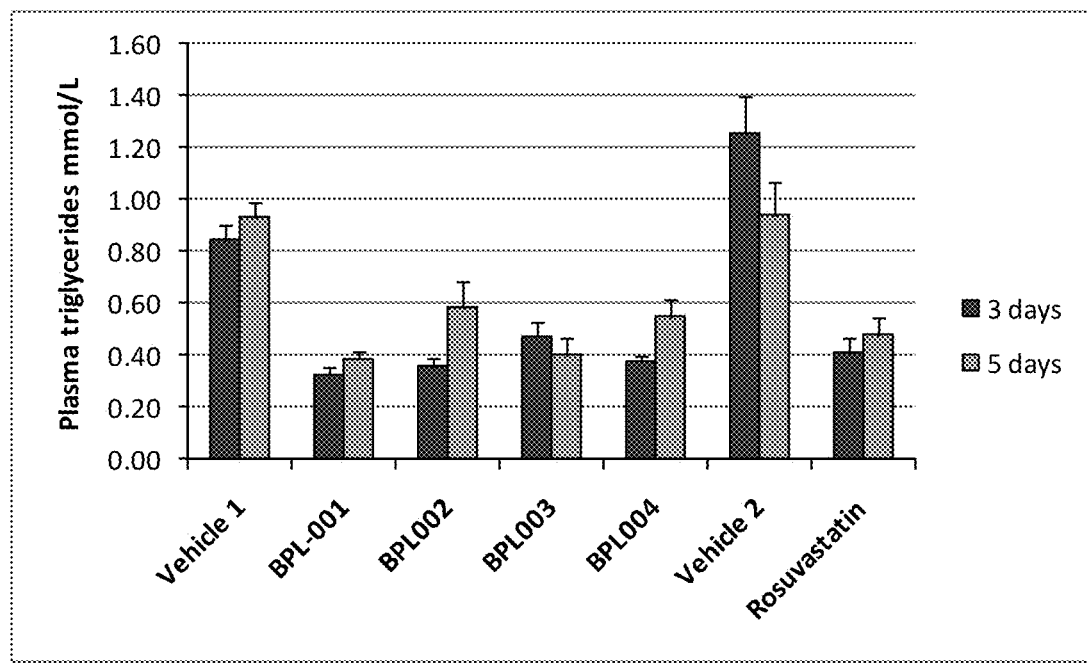

ROSUVASTATIN AND ATORVASTATIN DERIVATIVES

RELATED APPLICATIONS

This application is a continuation of U.S. patent application Ser. No. 13/255,700, filed Sep. 9, 2011, which is a national phase filing under 35 U.S.C. 371 of International Application No. PCT/GB2010/050407, filed Mar. 10, 2010 and claims the benefit of and priority to United Kingdom Patent Application No. GB0904104.7 filed on Mar. 10, 2009, the contents of which applications are herein incorporated by reference in their entirety.

FIELD OF THE INVENTION

The present invention relates to novel rosuvastatin and atorvastatin lactol derivatives.

BACKGROUND

Rosuvastatin, 7-[4-(4-fluorophenyl)-6-(1-methylethyl)-2-(methyl-methylsulfonyl-amino)-pyrimidin-5-yl]-3,5-dihydroxy-hept-6-enoic acid, and its use in the inhibition of the biosynthesis of cholesterol was first disclosed in EP 0521471. Rosuvastatin is a potent inhibitor of HMG-CoA enzyme.

Trans-6-[2-(3- or 4-carboxamido-substituted pyrrol-1-yl) alkyl]-4-hydroxypyran-2-one compounds are lactones which were first disclosed in U.S. Pat. No. 4,681,893. This document also disclosed their corresponding ring opened acid equivalents i.e. atorvastatin and its analogues which have activity as HMG-CoA inhibitors. The lactone compounds, however, apparently do not have intrinsic activity of their own. The corresponding ring-opened acid equivalents are useful as cholesterol biosynthesis inhibitors because of their HMG-CoA activity. Also disclosed in U.S. Pat. No. 4,681,893 are various methods of manufacture for such compounds.

Atorvastatin, which is the R form of the ring-opened acid of trans-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide, and its use in the inhibition of the biosynthesis of cholesterol was first disclosed in EP 0409281. Atorvastatin both in racemic form, and in the form of its [R—(R*,R*)] isomer is a potent inhibitor of HMG-CoA enzyme.

Clin Invest Med, Volume 24, No 5, p258-72, 2001 (Baker and Tamopolsky) discloses that whilst statins having an open, hydroxy acid conformation are active, the lactone, closed-ring analogue is inactive. Hepatic hydrolysis at alkaline pH decyclises and hence activates the lactone prodrugs lovastatin and simvastatin in vivo by formation of the active ring opened species. However, one problem with such compounds is that extensive first path metabolism leads to rapid clearance of the resulting ring opened statin.

Similarly, Trends in Pharmacological Sciences, Volume 19, Issue 1, 1 Jan. 1998, Pages 26-37 discloses that the inactive lactones must be metabolised to their corresponding open hydroxy acid forms in order to inhibit HMG-CoA reductase.

The lactone form, and also the ring opened active form, may also suffer problems in terms of stability over an extended period of time. This represents a significant problem during manufacture of an active principal or during extended storage of the same in a pharmacy. For example, loss of the hydroxy group in a dehydration reaction may occur. The resulting decomposition product may have a double bond that is conjugated with the lactone carbonyl group and this will tend to favour the potential decomposition product. Equally, in the ring opened form, one of the possible decomposition products could also have a conjugated double bond with the acid carbonyl group.

BRIEF SUMMARY

It is therefore an aim of the present invention to provide pharmaceutically active novel rosuvastatin and atorvastatin lactol derivatives. It is also an aim to provide compounds having improved stability. Ideally, the compounds will have an extended shelf-life. It is an aim of the invention to provide compounds that can be prepared by synthetic methods that are susceptible to industrial scale up. It is also an aim of the invention to provide compounds that can be prepared economically and reliably. It is also an aim to provide compounds which have good solubility and/or bioavailability. This invention provides compounds that achieve one or more of the above aims.

According to one aspect, the present invention provides a compound of Formula I and pharmaceutically acceptable salts and solvates thereof:

(I)

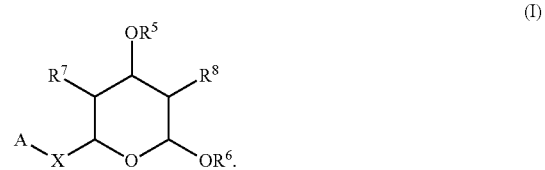

wherein:
A is selected from the group comprising:

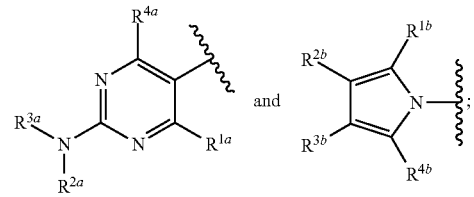

$R^{1a}$, $R^{4a}$, $R^{1b}$, $R^{4b}$ and one of $R^{2b}$ and $R^{3b}$ are each independently selected from the group comprising: hydrogen, halo, $C_{1-6}$ alkyl, $C_{2-6}$ alkenyl, $C_{3-6}$ cycloalkyl, aryl, $C_{1-4}$ alkyl aryl, heterocyclyl, and $C_{1-4}$ alkyl heteroaryl;

$R^{2a}$ is —S(O)$_2$R$^{9a}$ wherein $R^{9a}$ is $C_{1-6}$ alkyl, $C_{3-6}$ cycloalkyl, $C_{1-6}$ alkyl aryl or aryl;

$R^{3a}$ is hydrogen, $C_{1-6}$ alkyl, $C_{2-6}$ alkenyl, $C_{3-6}$ cycloalkyl or aryl;

and the other of $R^{2b}$ and $R^{3b}$ is —CONR$^{9b}$R$^{10b}$ where $R^{9b}$ and $R^{10b}$ are independently selected from the group comprising: hydrogen, $C_{1-6}$ alkyl, $C_{2-6}$ alkenyl, aryl, $C_{1-4}$ alkyl aryl, heteroaryl, heteroaryl;

$R^5$ and $R^6$ are independently selected from the group comprising: hydrogen, $C_{1-6}$ alkyl, $C_{1-6}$ haloalkyl, $C_{2-6}$ alkenyl, $C_{3-6}$ cycloalkyl, aryl, $C_{1-6}$ alkyl aryl, $C_{1-6}$alkanoyl aryl, heteroaryl, $C_{1-6}$alkanoyl heteroaryl and $C_{1-6}$ alkyl heteroaryl; provided always that both $R^5$ and $R^6$ are not hydrogen; and provided that $R^5$ is not benzyl or H when $R^6$ is methyl.

$R^7$ and $R^8$ are independently selected from the group comprising: H, $C_{1-4}$ alkyl and halo;

X is —(CR$^a$R$^b$)$_m$(CR$^a$=CR$^b$)$_n$(CR$^a$R$^b$)$_o$— where $R^a$ and $R^b$ are independently selected from the group comprising: H, methyl, ethyl and halo and m, n, and o are independently 0, 1, 2, or 3 provided that m+n+o is not more than 3; and wherein each of the above R groups may, where chemically possible, be independently optionally substituted by from 1 to 5 groups chosen independently at each occurrence from the groups comprising: halo, $C_{1-3}$ alkyl, halo $C_{1-3}$ alkyl, $C_{1-3}$ alkoxy, $C_{1-3}$ haloalkoxy, hydroxy, and cyano.

The compounds of the invention may have activity in their own right or may in certain cases ring open under physiological conditions to corresponding compounds having inhibitory activity.

BRIEF DESCRIPTION OF THE DRAWINGS

Reference is made to the accompanying FIGURE (FIG. 1) which illustrates the effect on the level of plasma triglycerides in rats after administration of rosuvastatin (25 mg/kg po) and four rosuvastatin analogues (25 mg/kg).

DETAILED DESCRIPTION

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (1) may be prepared by one or more of three methods:
(i) by reacting the compound of formula (1) with the desired acid or base;
(ii) by removing an acid- or base-labile protecting group from a suitable precursor of the compound of formula (1) or by ring-opening a suitable cyclic precursor, for example, a lactone or lactam, using the desired acid or base; or
(iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labelled compounds of formula (1).

Before purification, the compounds of the present invention may exist as a mixture of enantiomers depending on the synthetic procedure used. For example, the compounds of the present invention may exist as a mixture of enantiomers having a ratio of between 2:1 and 3:1, though they may also occur in other ratios. The enantiomers can be separated by conventional techniques known in the art. Thus the invention covers individual enantiomers as well as mixtures thereof. When the chemical structures disclosed herein includes an '*', it is intended that the compound is a mixture of enantiomers having a ratio of between 2:1 and 3:1.

For some of the steps of the process of preparation of the compounds of formula (1), it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of formula (1) as well as intermediate for the preparation thereof can be purified according to various well-known methods, such as for example crystallization or chromatography.

We have found that compounds of the invention enjoy good activity as HMG-CoA inhibitors. The compounds are sparingly soluble in water and are thus available for metabolism. In this regard, despite the presence of a bulky group at the 2-position of the lactol derivative, the compounds will still metabolise by loss of the substituent group, oxidation and subsequent ring opening to form HMG-CoA inhibitors. Furthermore, the compounds have intrinsic activity in their own right. Both of these findings are unexpected and counterintuitive. It is therefore expected that the compounds will show a more stable release profile in vivo. It is also expected that the compounds may have a longer half-life and/or an extended duration of action. This is surprising because these types of closed ring compounds are not expected to have activity at all.

Furthermore, the presence of a substituent group might be expected to be a barrier to oxidation and subsequent transformation to a useful active compound by ring opening.

In an embodiment, $R^6$ is selected from the group comprising: $C_{2-6}$ alkyl, $C_{2-6}$ alkenyl, $C_{3-6}$ cycloalkyl, aryl, $C_{1-6}$ alkyl aryl, heteroaryl, and $C_{1-6}$ alkylheteroaryl.

In an embodiment, A is:

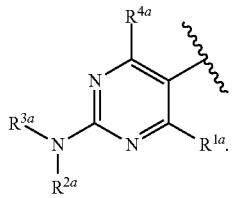

In an alternative embodiment, A is:

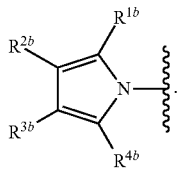

In an embodiment, $R^{1a}$ and $R^{1b}$ are each independently selected from the group comprising: hydrogen, $C_{1-6}$ alkyl, $C_{2-6}$ alkenyl or $C_{3-6}$ cycloalkyl. In an embodiment, $R^{1a}$ and $R^{1b}$ are each independently selected from the group comprising: $C_{2-6}$ alkenyl or $C_{3-6}$ cycloalkyl. In an alternative embodiment, $R^{1a}$ and $R^{1b}$ are each independently $C_{1-6}$ alkyl. In an embodiment, $R^{1a}$ and $R^{1b}$ are each independently methyl, ethyl, propyl or butyl. In an embodiment, $R^{1a}$ and $R^{1b}$ are i-propyl.

In an embodiment, $R^{2a}$ is —S(O)$_2$R$^{9a}$ wherein $R^{9a}$ is $C_{1-6}$ alkyl. In an embodiment, $R^{2a}$ is —S(O)$_2$R$^{9a}$ wherein $R^{9b}$ is methyl, ethyl, propyl or butyl. In an embodiment, $R^{2a}$ is —S(O)$_2$Me.

In an embodiment, $R^{2b}$ is —CONR$^{9b}$R$^{10b}$ where $R^{9b}$ is hydrogen or $C_{1-4}$ alkyl, preferably hydrogen; and $R^{10b}$ is selected from the group comprising: aryl, $C_{1-4}$ alkyl aryl, heteroaryl and $C_{1-4}$ alkyl heteroaryl, preferably $R^{10b}$ is selected from the group comprising: aryl and $C_{1-4}$ alkyl aryl. In an embodiment, $R^{10b}$ is phenyl.

In an embodiment, $R^{3a}$ is selected from the group comprising: hydrogen, $C_{1-6}$ alkyl and $C_{3-6}$ cycloalkyl. In an embodiment, $R^{3a}$ is selected from the group comprising: hydrogen and $C_{1-6}$ alkyl. In an embodiment, $R^{3a}$ is methyl, ethyl or propyl. In an embodiment, $R^{3a}$ is methyl.

In an embodiment, $R^{3b}$ is selected from the group comprising: aryl, $C_{1-4}$ alkyl aryl, heteroaryl and $C_{1-4}$ alkyl heteroaryl. In an embodiment, $R^{3b}$ is selected from the group comprising: aryl and $C_{1-4}$ alkyl aryl. In an embodiment, $R^{3b}$ is aryl. In an embodiment, $R^{3b}$ is phenyl.

In an embodiment, $R^{4a}$ and $R^{4b}$ are each independently selected from the group comprising: aryl, $C_{1-4}$ alkyl aryl, heteroaryl and $C_{1-4}$ alkyl heteroaryl, wherein each of the aforementioned groups may be optionally substituted as discussed above in relation to the first aspect. In an embodiment, $R^{4a}$ and $R^{4b}$ are each independently selected from the group comprising: aryl and $C_{1-4}$ alkyl aryl. In an embodiment, $R^{4a}$ and $R^{4b}$ are each independently aryl. In an embodiment, $R^{4a}$ and $R^{4b}$ are each phenyl. In an embodiment, $R^{4a}$ and $R^{4b}$ are each phenyl independently substituted with halo, optionally wherein the halo is fluorine. In an embodiment, $R^{4a}$ and $R^{4b}$ are each 4-fluorophenyl.

In an embodiment, $R^5$ is selected from the group comprising: hydrogen, $C_{1-6}$ alkyl, aryl, $C_{1-4}$ alkyl aryl, $C_{1-6}$alkanoyl aryl, heteroaryl, $C_{1-6}$alkanoyl heteroaryl and $C_{1-4}$ alkyl heteroaryl. In an embodiment, $R^5$ is selected from the group comprising: hydrogen, $C_{1-4}$ alkyl aryl and $C_{1-4}$ alkyl heteroaryl. In an embodiment, $R^5$ is $C_{1-4}$ alkyl aryl. In an embodiment, $R^5$ is $C_{1-6}$alkanoyl heteroaryl, e.g. methanoyl heteroaryl. In a preferred embodiment, $R^5$ is methanoyl pyridyl, e.g. 2-methanolyl pyridine, 3-methanolyl pyridine or 4-methanolyl pyridine, preferably 3-methanolyl pyridine. In an embodiment, $R^5$ is hydrogen. In an alternative embodiment, $R^5$ is benzyl.

In an embodiment, $R^6$ is selected from the group comprising: $C_{1-6}$ alkyl, $C_{1-6}$ haloalkyl, $C_{2-6}$ alkenyl, $C_{3-6}$ cycloalkyl and optionally substituted aryl.

In an embodiment, $R^6$ is $C_{1-6}$ alkyl. In an embodiment, $R^6$ is methyl, ethyl, propyl, n-propyl, iso-propyl, butyl, sec-butyl, iso-butyl or tert-butyl. In an embodiment, $R^6$ is methyl. In an embodiment, $R^6$ is iso-propyl or tert-butyl.

In an embodiment, $R^6$ is $C_{3-6}$ cycloalkyl. In a preferred embodiment, $R^6$ is cyclohexyl.

In an embodiment, $R^6$ is $C_{1-6}$ haloalkyl e.g. a $C_{1-6}$ chloroalkyl. In an embodiment, $R^6$ is chloroethyl.

In an embodiment, $R^6$ is $C_{2-6}$ alkenyl. In an embodiment, $R^6$ is prop-2-ene.

In an embodiment, $R^6$ is optionally substituted aryl. In an embodiment, $R^6$ is 2,4,6-trifluorophenyl or 2,4-dimethoxyphenyl.

In an embodiment, $R^7$ is H.

In an embodiment, $R^8$ is H.

In an embodiment, m=0, n=1 and o=0. In an embodiment, m=1, n=1 and o=0, or m=0, n=1 and o=1. In an embodiment, n is 0. In an embodiment, m=1, n=0 and o=1; m=2, n=0 and o=0; or m=0, n=0 and o=2. In an alternative embodiment, m=3, n=0 and o=0. In an alternative embodiment, m=1, n=0 and o=0.

In a preferred embodiment, X is

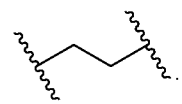 [SMILES: *CC*]

In an alternative preferred embodiment, X is

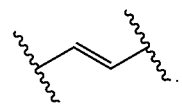

In an embodiment, $R^a$ is H at each occurrence.

In an embodiment, $R^b$ is H at each occurrence.

Preferably, when one or more of the above groups is substituted, each optional substituent is an independently chosen halo atom. Amongst halo, chloro and fluoro are preferred.

In an embodiment, $R^{1a}$ is $C_{1-4}$alkyl, preferably i-propyl, and $R^{4a}$ is optionally substituted aryl, preferably 4-fluorophenyl.

In an embodiment, $R^{1b}$ is $C_{1-4}$alkyl, preferably i-propyl, and $R^{4b}$ is optionally substituted aryl, preferably 4-fluorophenyl.

In another embodiment, $R^{2a}$ is —S(O)$_2$R$^{9a}$ wherein $R^{9b}$ is $C_{1-6}$ alkyl, preferably methyl, and $R^{3a}$ is hydrogen or $C_{1-6}$ alkyl, preferably methyl.

In another embodiment, $R^{2b}$ is —CONR$^{9b}$R$^{10b}$ wherein $R^{9b}$ is optionally substituted aryl, preferably phenyl; $R^{10b}$ is hydrogen; and $R^{3b}$ is optionally substituted aryl, preferably phenyl.

In an embodiment, $R^{1a}$ is $C_{1-4}$alkyl, preferably i-propyl; $R^{2a}$ is —S(O)$_2$R$^{9a}$ wherein $R^{9a}$ is $C_{1-6}$ alkyl, preferably methyl; $R^{3a}$ is hydrogen or $C_{1-6}$ alkyl, preferably methyl; and $R^{4a}$ is optionally substituted aryl, preferably 4-fluorophenyl.

In a further embodiment, $R^{1b}$ is $C_{1-4}$alkyl, preferably i-propyl; $R^{2b}$ is —CONR$^{9b}$R$^{10b}$ wherein $R^{9b}$ is optionally substituted aryl, preferably phenyl, $R^{10b}$ is hydrogen; $R^{3b}$ is optionally substituted aryl, preferably phenyl; and $R^{4b}$ is optionally substituted aryl, preferably 4-fluorophenyl.

In an embodiment, $R^5$ is hydrogen or optionally substituted benzyl; and $R^6$ is optionally substituted $C_{2-6}$alkyl, preferably propyl or butyl, or optionally substituted $C_{2-6}$alkenyl, preferably prop-2-ene. In a preferred embodiment, $R^5$ is benzyl and $R^6$ is $C_{2-6}$ alkyl, preferably propyl, iso-propyl, butyl, iso-butyl or tert-butyl. In a preferred embodiment, $R^5$ is benzyl and $R^6$ is $C_{2-6}$ alkenyl, preferably prop-2-ene. In a preferred embodiment, $R^5$ is benzyl and $R^6$ is $C_{2-6}$ haloalkyl, preferably 2,2,2-trichlororethyl. In a preferred embodiment, $R^5$ is hydrogen; and $R^6$ is optionally substituted aryl, preferably 2,4,6-trifluorophenyl or 2,4-dimethoxyphenyl. In a preferred embodiment, $R^5$ is hydrogen and $R^6$ is $C_{2-6}$ alkyl, preferably n-propyl. In a preferred embodiment, $R^5$ is hydrogen and $R^6$ is $C_{3-6}$ cycloalkyl, preferably cyclohexyl. In a preferred embodiment, $R^5$ is hydrogen; and $R^6$ is $C_{2-6}$ haloalkyl, preferably chloroethyl. In a preferred embodiment, $R^5$ is $C_{1-6}$alkanoyl heteroaryl and $R^6$ is $C_{1-6}$ alkyl, preferably methyl. In another preferred embodiment, $R^5$ is methanoyl pyridyl, e.g. 2-methanolyl pyridine, 3-methanolyl pyridine or 4-methanolyl pyridine, preferably 3-methanolyl pyridine and $R^6$ is $C_{1-6}$ alkyl, preferably methyl, ethyl or propyl.

Aryl groups include aromatic ring systems comprising 6, 7, 8, 9, 10, 11, 12, 13, 14, 15 or 16 ring carbon atoms. Aryl groups may consist of a single ring but may include a polycyclic ring system, having two or more rings, at least one of which is aromatic. Aryl groups include: phenyl, naphthyl, fluorenyl, azulenyl, indenyl and anthryl groups.

In an embodiment, the aryl group is phenyl.

Heteroaryl groups include aromatic heterocyclic ring systems having 5, 6, 7, 8, 9, 10, 11, 12, 13, 14, 15 or 16 ring atoms with 1 to 4 heteroatoms independently selected from nitrogen, oxygen and sulfur. The group may be a polycyclic ring system, having two or more rings, at least one of which is aromatic, but is more often monocyclic. Preferred heteroaryl groups are monocyclic groups containing 5 or 6 ring atoms. Heteroaryl groups include: pyrrolyl, pyrazolyl, imidazolyl, pyrazinyl, oxazolyl, isoxazolyl, thiazolyl, furyl, thiophenyl, pyridyl, pyrimidyl, benzimidazolyl, indolyl, isoquinolyl, quinoxalinyl and quinolyl.

In an embodiment, the heteroaryl group is selected from the group comprising: pyridine, pyrimidine, pyrazine, pyrazole, and oxazole. Preferably the heteroaryl group is pyridine.

In an embodiment, the compound has a structure selected from:

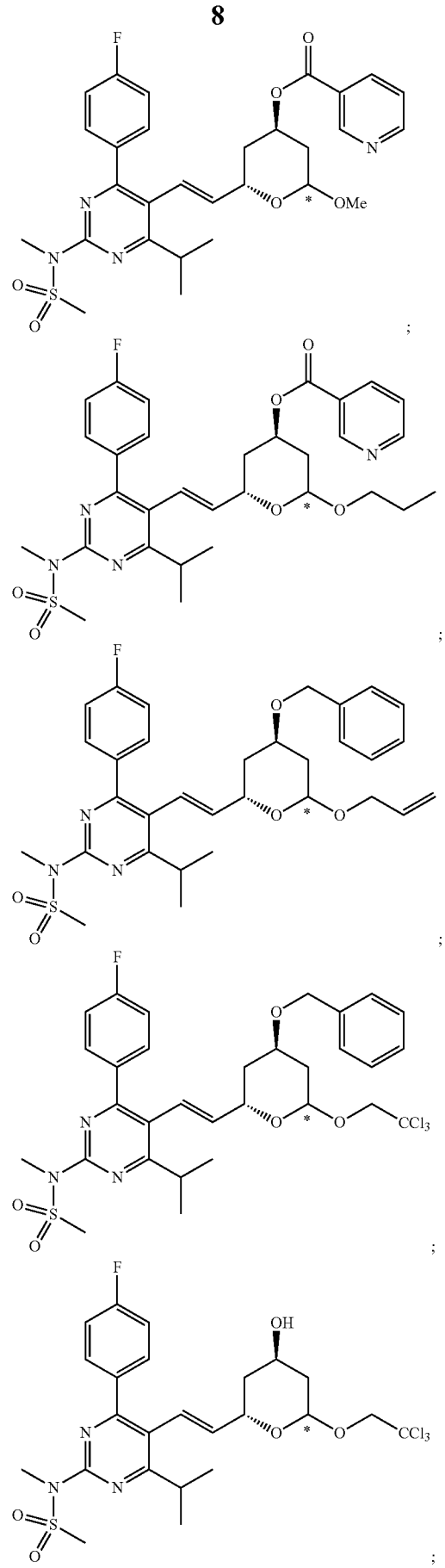

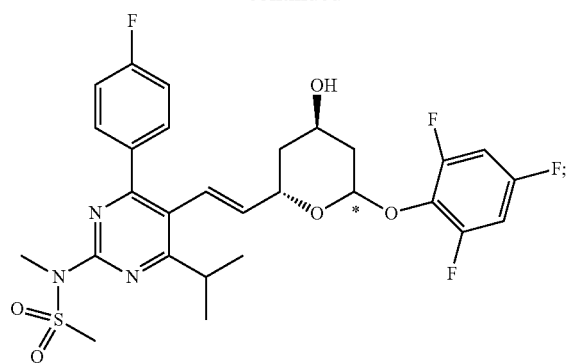
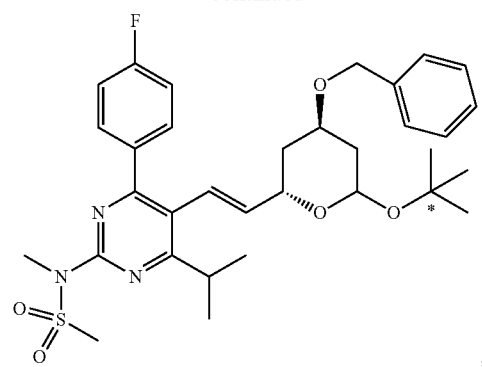
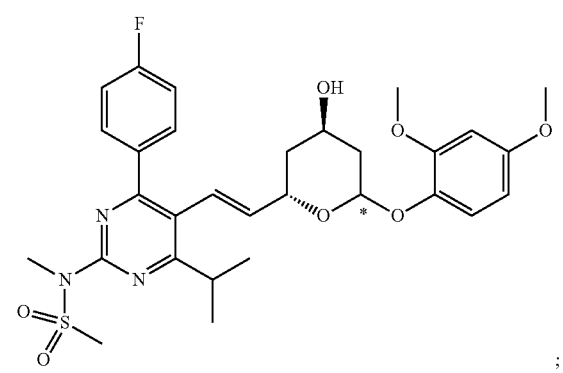
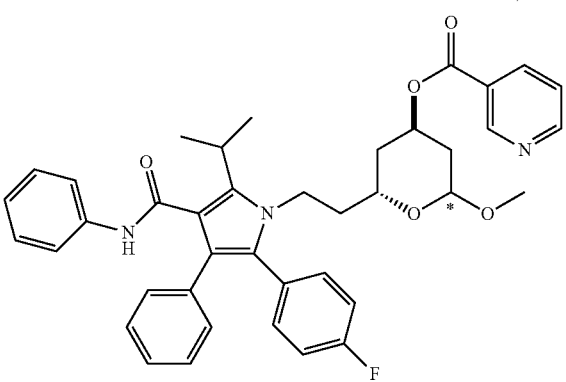
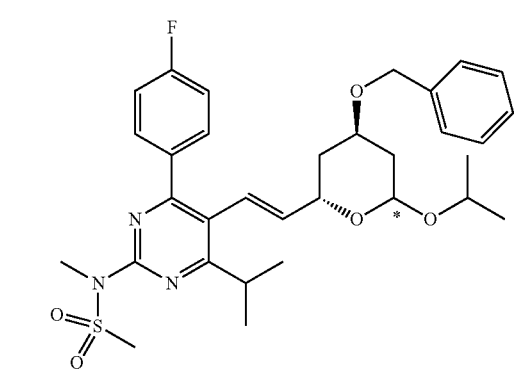
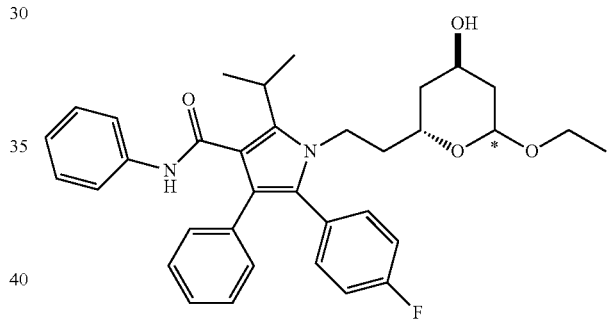
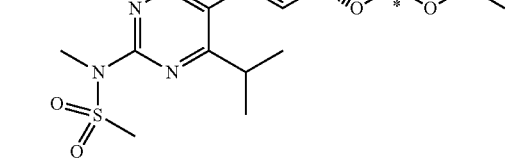
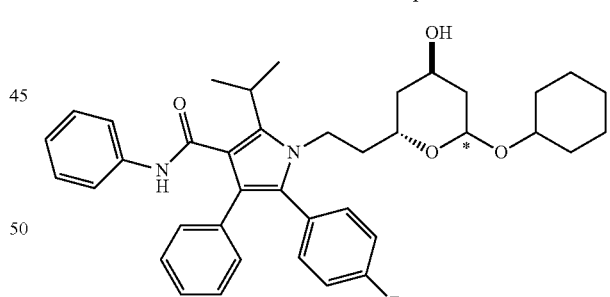
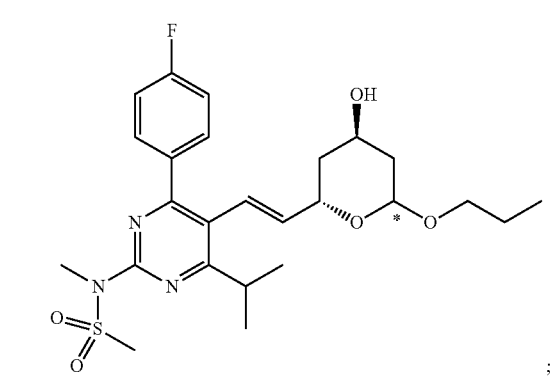
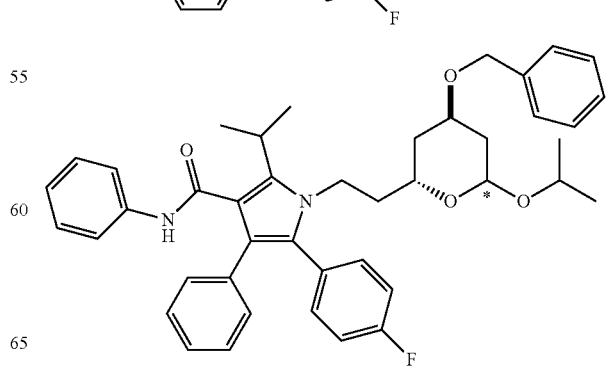

-continued

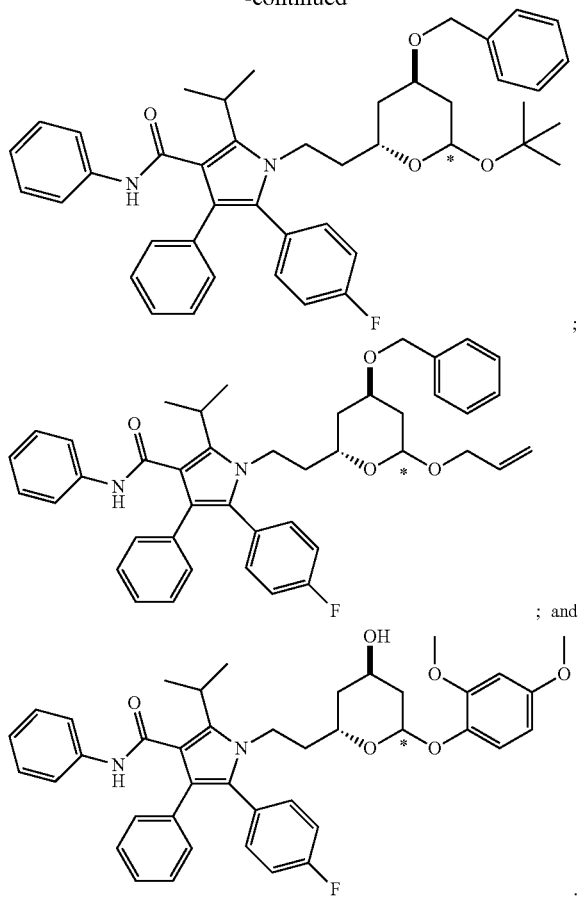

Processes for the manufacture of the compounds of the present invention are disclosed in WO2005/012246, in particular, in the examples. The disclosure of WO2005/012246 insofar as the synthetic procedures are concerned forms part of the disclosure of the present invention. In the interests of brevity, the details of these synthetic procedures is not reproduced here but it is intended that this subject matter is specifically incorporated into the disclosure of this document by reference.

In addition to the above aspects, the present invention may also relate to the use of rosuvastatin and atorvastatin lactol derivatives in the manufacture of a medicament for treating certain conditions. Conditions that are treatable using the compounds of the present invention include conditions which are modulated by the enzyme 3-hydroxy-3-methylglutaryl-coenzyme A reductase (HMG-CoA reductase). Inhibition of the enzyme therefore represents a viable therapy for a number of diseases.

Examples of conditions that may be treated by the inhibition of HMG-CoA reductase include hypercholesterolemia, atherosclerosis and hyperlipidemia. Statins have been used in the secondary prevention of cardiovascular disease, or in the primary prevention of cardiovascular disease when the risk for cardiovascular disease is significantly raised. It is therefore expected that the compounds of the present invention will have utility in the treatment or prevention of cardiovascular diseases due to their inhibitory activity. Example cardiovascular diseases which may be treatable by the compounds of the present invention include: coronary heart disease, myocardial infarction, stroke and peripheral artery disease. In addition, these compounds may also have a beneficial effect in the treatment of inflammation, dementia, cancer, nuclear cataracts, diabetes and hypertension.

The conditions that may be treated by the inhibition of HMG-CoA reductase may be a condition of the human or animal body. These compounds are intended in particular for human patients.

The atorvastatin derivatives of the present invention can be assayed using the following procedure in which the plasma triglyceride level is measured after treating a rat with a compound of the present invention (or atorvastatin). The change in rat plasma triglyceride levels is considered to be a fair test for determining HMG CoA reductase activity.

The procedure used is as follows: male SD rats (Harlan) are housed in groups of 6 under a 12 h light dark cycle (lights on 07.00 h) with free access to food (normal laboratory chow) and water. Animals between 148-183 g are allocated to treatment groups of 8 balanced by body weight and treatments are balanced across cages.

Solutions including 5 mg/mL of the atorvastatin analogues (in e.g. 10% PEG300/10% cremophor/80% methyl cellulose (0.5%)) and a suspension including 5 mg/kg of atorvastatin (formulated in 0.5% Tween in 0.5% methyl cellulose) are made.

The rat subjects are orally dosed with one of the atorvastatin analogues (25 mg/kg) or atorvastatin (25 mg/kg po), BID for 3 or 5 days.

Sixteen hours after the last treatment, terminal plasma samples are taken, stored at −20° C., and transported on dry ice for analysis of triglyceride levels.

Data for each time-point are analysed by 1-way ANOVA and post-hoc Dunnett's test.

The present invention also includes the synthesis of all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

General Procedure

All assays were carried out in a reaction buffer containing 100 nM $K_xPO_4$ at pH 7.2, 1 mM EDTA, 500 mM KCl and 1 mg/ml BSA. The concentrations of NADPH and HMG-CoA were both 200 µM. The enzyme concentration used is unknown although this concentration is 10-fold lower than that of the stock solution purchased. Inhibitors were dissolved in 75% DMSO. Where inhibitors were found to be insoluble or only partly soluble in 75% DMSO, 100% DMSO was used. Reactions were activated by the addition of enzyme and agitated for 12 seconds following the addition. Absorbance readings were then taken every 20 seconds for 600 seconds. In initial tests the concentration of each inhibitor was set at 50 nM to identify which compounds were the better inhibitors, compared to the known Pravastatin inhibitor. After these were identified, assays were carried out varying their concentrations from OnM to 50 nM allowing 1050 values to be calculated.

EXAMPLE 1

The following procedure was followed using a HMG-CoA Reductase assay kit obtained from Sigma-Aldrich (catalogue number CS1090). The assay is based on the spectrophotometric measurement of the decrease in absorbance at 340 nm of NADPH in solution. A decrease in absorbance is caused by the oxidation of NADPH by the catalytic subunit of HMGR in the presence of the substrate HMG-CoA. Effective inhibition of the HMG-CoA leads to a reduction in oxidation of NADPH which in turn leads to a smaller reduction in the absorbance at 340 nm over time. This is illustrated in the following reaction scheme:

HMG-CoA+2NADPH+2H$^+$→mevalonate+2NADP$^+$+ CoA-SH

Compounds showing the best inhibitory action are those which reduce the absorbance least.

Preparation of the Assay Solution

Ultrapure water (17 MΩ-cm or equivalent was used for the preparation of reagents and throughout the procedure.

First, an assay buffer solution was prepared using the following method: 0.2 ml of assay buffer, 5× (catalogue number A5981) was diluted with 0.8 ml of ultrapure water. The resulting buffer solution was kept on ice or stored at −20° C. for further use.

Next, 25 mg of NADPH (catalogue number $N_{65}O_5$) was reconstituted with 1.5 ml of the buffer solution. The reconstituted NADPH was stored in working aliquots at −20° C.

The HMG-CoA substrate solution (catalogue number S7447), HMG-CoA reductase (catalogue number H8789) and inhibitor solution (e.g. pravastatin, catalogue number I5909) were kept on ice throughout the procedure.

1. Before beginning, the spectrophotometer was set at 37° C. and 340 nm, with a kinetic programme: 1 ml sample, read every 20 seconds for up to 10 minutes.

2. The appropriate volumes of the reaction solutions were added according to Table 1 (1 ml assay).

TABLE 1

| | Reaction volumes for 1 ml samples | | | | |
|---|---|---|---|---|---|
| Sample | 1× Assay buffer | Test compound/ Pravastatin | NADPH | HMG-CoA | HGMG |
| Blank | 920 µl | — | 20 µl | 60 µl | — |
| Activity | 915 µl | — | 20 µl | 60 µl | 5 µl |
| Inhibition | 910 µl | 5 µl | 20 µl | 60 µl | 5 µl |

The reagents were added to the reaction in the following order:

a. Add a buffer to all samples.

b. Add the inhibitor (test compound/Pravastatin) to the inhibition sample.

c. Add the reconstituted NADPH to all samples.

d. Add Substrate Solution (HMG-CoA) to all samples.

e. Add HMG-CoA Reductase (HMGR) to the Activity and Inhibition samples.

f. Mix the samples thoroughly.

3. The kinetics programme was started immediately. The activity of the product was calculated according to the following equation:

$$\text{Units/mg } P = \frac{(\Delta A_{340}/\min_{sample} - \Delta A_{340}/\min_{control})}{12.44 \times V \times 0.6 \times LP} \times TV$$

where:

12.44=$\epsilon^{mM}$—the extinction coefficient for NADPH at 340 nm is 6.22 mM$^{-1}$cm$^{-1}$. 12.44 represents the 2 NADPH consumed in the reaction.

TV=total volume of the reaction in ml (1 ml for cuvettes)

V=volume of enzyme used in the assay (ml)

0.6=enzyme concentration in mg-protein (mgPO/ml (0.55-0.65 mgP/ml)

LP=light path in cm (1 for cuvettes).

EXAMPLE 2

The following table provides IC50 values for particular rosuvastatin compounds of the present invention.

| Compound Structure | IC₅₀ (nM) |
|---|---|
| 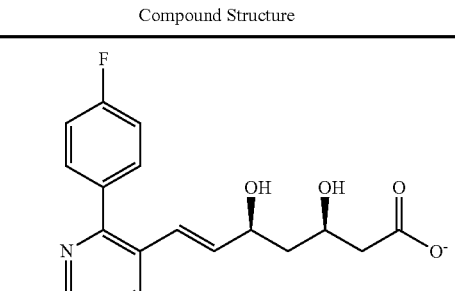 Rosuvastatin Ca²⁺ Salt | 4 |
| (4-fluorophenyl pyrimidine methylsulfonamide vinyl tetrahydropyran methoxy nicotinate) | <1 |
| (4-fluorophenyl pyrimidine methylsulfonamide vinyl tetrahydropyran propoxy nicotinate) | 8 |
| (4-fluorophenyl pyrimidine methylsulfonamide vinyl tetrahydropyran isopropoxy benzyloxy) | 1 |

| Compound Structure | IC₅₀ (nM) |
|---|---|
| (4-fluorophenyl pyrimidine methylsulfonamide vinyl tetrahydropyran t-butoxy benzyloxy) | 4 |
| (4-fluorophenyl pyrimidine methylsulfonamide vinyl tetrahydropyran allyloxy benzyloxy) | 3 |
| (4-fluorophenyl pyrimidine methylsulfonamide vinyl tetrahydropyran OCH₂CCl₃ benzyloxy) | 2 |
| (4-fluorophenyl pyrimidine methylsulfonamide vinyl tetrahydropyran 2,4,6-trifluorophenoxy hydroxy) | 1 |

EXAMPLE 3
The following table provides IC50 values for particular atorvastatin compounds of the present invention.
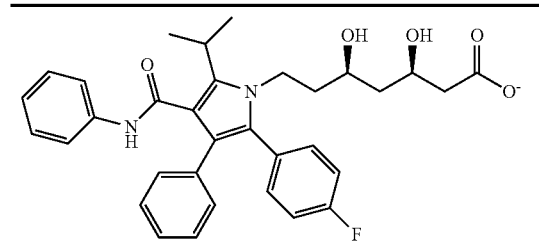

-continued

| Compound Structure | IC$_{50}$ (nM) |
|---|---|
| 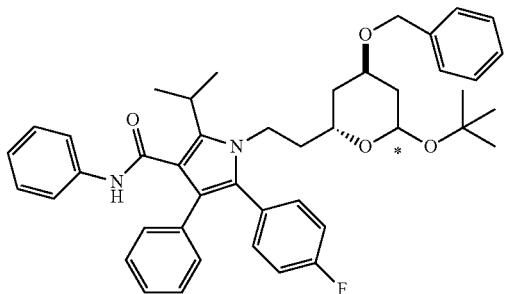 | 3 |
| 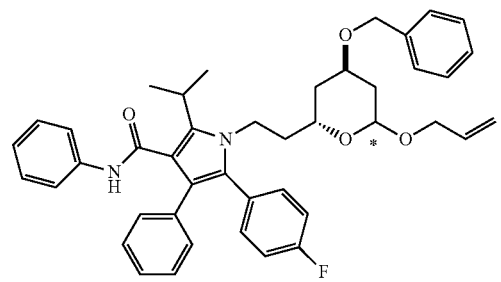 | 1 |
| 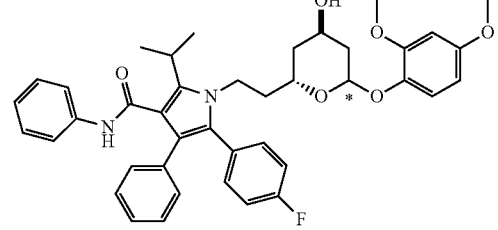 | <1 |

Example 4

The following example demonstrates the efficacy of the rosuvastatin compounds of the invention. The Example demonstrates the effect of 3 or 5 days BID treatment with four rosuvastatin compounds of the present invention and rosuvastatin (all at 25 mg/kg po) on rat plasma triglyceride levels 16 hours after the last treatment dose. The measurement of the change in rat plasma triglyceride levels is considered to be a fair test for determining HMG CoA reductase activity.

112 male SD rats (Harlan) were housed in groups of 6 under a 12 h light dark cycle (lights on 07.00 h) with free access to food (normal laboratory chow) and water. Animals between 148-183 g were allocated to treatment groups of 8 balanced by body weight and treatments were balanced across cages.

Four rosuvastatin analogues were made up in 10% PEG300/10% cremophor/80% methyl cellulose (0.5%) (vehicle 1) to make a 5 mg/mL solution. The rosuvastatin compounds used were:

Rosuvastatin Lactol n-propyl acetal (diastereomeric ratio 2/1) (BPL001); Rosuvastatin lactol n-propyl acetal nicotinoyl ester (diastereomeric ratio 2/1) (BPL002); Rosuvastatin lactol iso-propyl acetal benzyl ether (BPL003); and Rosuvastatin lactol methyl acetal nicotinoyl ester (diastereomeric ratio 2/1) (BPL004).

Rosuvastatin was formulated in 0.5% Tween in 0.5% methyl cellulose (vehicle 2) at 5 mg/kg as a suspension.

Rats were orally dosed with vehicle 1, one of the four rosuvastatin analogues in vehicle 1 (25 mg/kg), vehicle 2 or rosuvastatin in vehicle 2 (25 mg/kg po), BID for 3 or 5 days.

Sixteen hours after the last treatment, terminal plasma samples were taken, stored at −20° C., and transported on dry ice for analysis of triglyceride levels.

Data for each time-point were analysed by 1-way ANOVA and post-hoc Dunnett's test.

The results are provided in FIG. 1 from which it can be deduced that administration of rosuvastatin (25 mg/kg po) BID for 3 or 5 days causes a marked reduction in plasma triglycerides. All four rosuvastatin analogues also significantly reduced plasma triglycerides after both 3 and 5 days BID treatment. All animals tolerated the rosuvastatin treatments well and there was no evidence of any adverse events.

The magnitude of the effect of the rosuvastatin analogues was equivalent to that of rosuvastatin.

The invention claimed is:

1. A pharmaceutical composition comprising a composition of Formula I or a pharmaceutically acceptable salt or solvate thereof and a vehicle:

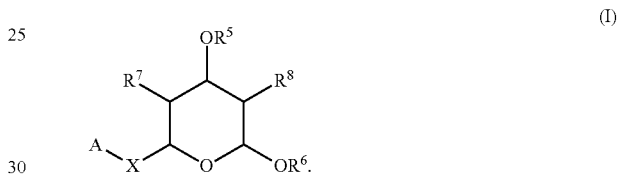

(I)

wherein:
A is

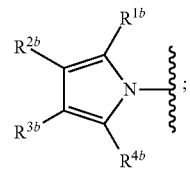

$R^{1b}$, $R^{4b}$ and one of $R^{2b}$ and $R^{3b}$ are each independently selected from the group consisting of: hydrogen, halo, $C_{1-6}$ alkyl, $C_{2-6}$ alkenyl, $C_{3-6}$ cycloalkyl, aryl, $C_{1-4}$ alkyl aryl, heterocyclyl, and $C_{1-4}$ alkyl heteroaryl;
and the other of $R^{2b}$ and $R^{3b}$ is —CONR$^{9b}$R$^{10b}$ where $R^{9b}$ and $R^{10b}$ are independently selected from the group consisting of: hydrogen, $C_{1-6}$ alkyl, $C_{2-6}$ alkenyl, aryl, $C_{1-4}$ alkyl aryl, heteroaryl, and $C_{1-4}$ heteroaryl;
$R^5$ is selected from the group consisting of: hydrogen, $C_{1-6}$ alkyl, $C_{1-6}$ haloalkyl, $C_{2-6}$ alkenyl, $C_{3-6}$ cycloalkyl, aryl, $C_{1-6}$ alkyl aryl, $C_{1-6}$ alkanoyl aryl, heteroaryl, $C_{1-6}$ alkanoyl heteroaryl and $C_{1-6}$ alkyl heteroaryl;
$R^6$ is selected from the group consisting of: $C_{2-6}$ alkyl, $C_{2-6}$ alkenyl, $C_{3-6}$ cycloalkyl, aryl, heteroaryl and $C_{1-6}$ alkyl heteroaryl;
$R^7$ and $R^8$ are independently selected from the group consisting of: H, $C_{1-4}$ alkyl and halo;
X is —(CR$^a$R$^b$)$_m$(CR$^a$=CR$^b$)$_{n}$(CR$^a$R$^b$)$_o$— where $R^a$ and $R^b$ are independently selected from the group consisting of: H, methyl, ethyl and halo and m, n, and o are independently 0, 1, 2, or 3 provided that m+n+o is not more than 3; and wherein
each of the above R groups may, where chemically possible, be independently optionally substituted by from 1 to 5 groups chosen independently at each occurrence from the groups consisting of: halo, $C_{1-3}$ alkyl, halo $C_{1-3}$ alkyl, $C_{1-3}$ alkoxy, $C_{1-3}$ haloalkoxy, hydroxy, and cyano.

2. The composition of claim 1, wherein $R^{1b}$ is $C_{1-6}$ alkyl.

3. The composition of claim 1, wherein $R^{2b}$ is —$CONR^{9b}R^{10b}$ where $R^{9b}$ is H and $R^{10b}$ is aryl.

4. The composition of claim 1, wherein $R^{3b}$ is aryl.

5. The composition of claim 1, wherein $R^{4b}$ is optionally substituted aryl.

6. The composition of claim 1, wherein $R^{1b}$ is i-propyl, $R^{2b}$ is —CONHPh, $R^{3b}$ is phenyl and $R^{4b}$ 4-fluorophenyl.

7. The composition of claim 1, wherein $R^5$ is selected from the group consisting of: hydrogen, $C_{1-6}$ alkyl, aryl, $C_{1-6}$ alkyl aryl, $C_{1-6}$ alkanoyl aryl, heteroaryl, $C_{1-6}$ alkanoyl heteroaryl and $C_{1-6}$ alkyl heteroaryl.

8. The composition of claim 7 wherein $R^5$ is hydrogen.

9. The composition of claim 7, wherein $R^5$ is selected from the group comprising:
—$C_1$ alkyl-Ph, —$C_2$ alkyl-Ph, —$C_3$ alkyl-Ph, and —$C_4$ alkyl-Ph.

10. The composition of claim 9, wherein $R^5$ is benzyl.

11. The composition of claim 7, wherein $R^5$ is $C_{1-6}$ alkanoyl pyridine.

12. The composition of claim 11, wherein $R^5$ is 3-methanoyl pyridine.

13. The composition of claim 1, wherein $R^6$ is selected from the group consisting of: $C_{2-6}$ alkyl, $C_{1-6}$ haloalkyl, $C_{2-6}$ alkenyl, $C_{3-6}$ cycloalkyl, aryl, heteroaryl and $C_{1-6}$ alkyl heteroaryl.

14. The composition of claim 13, wherein $R^6$ is selected from the group consisting of: ethyl, propyl, butyl, chloromethyl, chloroethyl, chloropropyl, chlorobutyl and propylene.

15. The composition of claim 1, wherein $R^6$ is optionally substituted aryl.

16. The composition of claim 15, wherein $R^6$ is selected from the group consisting of: $C_{1-6}$ alkoxy substituted phenyl and halo substituted phenyl.

17. The composition of claim 16, wherein $R^6$ is selected from the group consisting of: 2,4,6-trifluorophenyl and 2,4-dimethoxyphenyl.

18. The composition of claim 1, wherein $R^6$ is selected from the group consisting of: $C_{2-6}$ alkyl, $C_{3-6}$ cycloalkyl, $C_{2-6}$ alkenyl and aryl.

19. The composition of claim 18, wherein $R^6$ is selected from the group consisting of: ethyl, propyl, butyl, cyclohexyl and allyl.

20. The composition of claim 1, wherein $R^5$ is hydrogen and $R^6$ is an optionally substituted aromatic group.

21. The composition of claim 1, wherein $R^5$ is an optionally substituted benzyl and $R^6$ is an optionally substituted $C_{2-6}$ alkyl, an optionally substituted $C_{2-6}$ alkenyl or a $C_{1-6}$ haloalkyl.

22. The composition of claim 1, wherein $R^5$ is a $C_{1-6}$ alkanoyl heteroaryl and $R^6$ is an optionally substituted $C_{2-6}$ alkyl.

23. The composition of claim 1, wherein $R^5$ is hydrogen and $R^6$ is an $C_{2-6}$ alkyl, $C_{3-6}$cycloalkyl or an optionally substituted aryl.

24. The composition of claim 1, wherein $R^7$ is H and $R^8$ is H.

25. The composition of claim 1, wherein $R^a$ is H, $R^b$ is H and m=0, n=1 and o=0; or
each $R^a$ is H, each $R^b$ is H and m=2, n=0 and o=0.

26. The composition of claim 1 in which the composition of Formula I has a structure selected from:

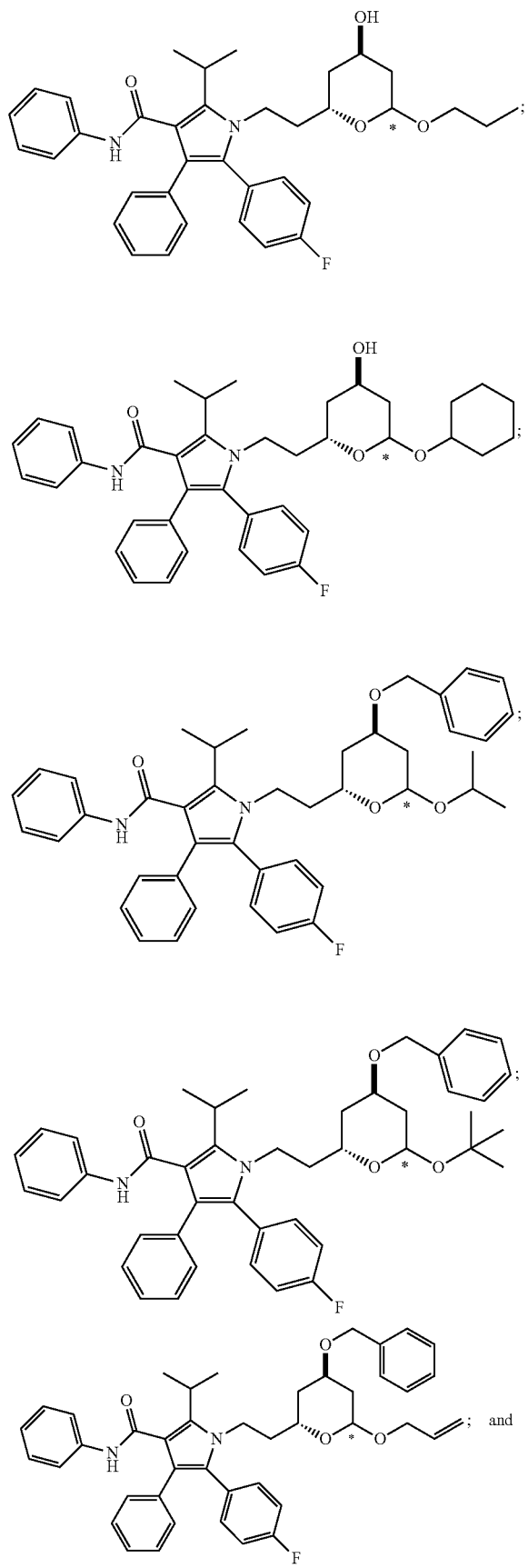

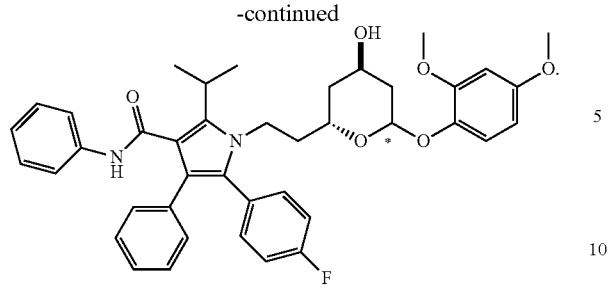
* * * * *